US010662260B2

(12) United States Patent
Ling et al.

(10) Patent No.: US 10,662,260 B2
(45) Date of Patent: May 26, 2020

(54) CYCLODEXTRIN-BASED POLYANIONIC AND NON-IONIC DENDRIMERS

(71) Applicant: UTI Limited Partnership, Calgary (CA)

(72) Inventors: Chang-Chun Ling, Calgary (CA); Ping Zhang, Calgary (CA)

(*) Notice: Subject to any disclaimer, the term of this patent is extended or adjusted under 35 U.S.C. 154(b) by 0 days.

(21) Appl. No.: 15/314,266

(22) PCT Filed: Mar. 31, 2015

(86) PCT No.: PCT/CA2015/050254
§ 371 (c)(1),
(2) Date: Nov. 28, 2016

(87) PCT Pub. No.: WO2015/179963
PCT Pub. Date: Dec. 3, 2015

(65) Prior Publication Data
US 2017/0107304 A1    Apr. 20, 2017

Related U.S. Application Data

(60) Provisional application No. 62/060,787, filed on Oct. 7, 2014, provisional application No. 62/004,364, filed on May 29, 2014.

(51) Int. Cl.
| | |
|---|---|
| *C08B 37/16* | (2006.01) |
| *C08L 5/16* | (2006.01) |
| *A61K 47/40* | (2006.01) |
| *C08G 83/00* | (2006.01) |
| *C08G 81/00* | (2006.01) |

(52) U.S. Cl.
CPC .......... *C08B 37/0012* (2013.01); *A61K 47/40* (2013.01); *C08B 37/0015* (2013.01); *C08G 81/00* (2013.01); *C08G 83/003* (2013.01); *C08L 5/16* (2013.01); *C08L 2203/02* (2013.01)

(58) Field of Classification Search
None
See application file for complete search history.

(56) References Cited

U.S. PATENT DOCUMENTS

| | | | |
|---|---|---|---|
| 6,670,340 B1 | 12/2003 | Zhang et al. | |
| 7,332,149 B1 | 2/2008 | Rajopadhye et al. | |
| 7,632,941 B2 | 12/2009 | Defaye | |
| 8,492,538 B1 | 7/2013 | Matos | |
| 9,066,970 B2 | 6/2015 | Fichert et al. | |
| 2009/0270348 A1 | 10/2009 | Antle | |
| 2010/0056475 A1 | 3/2010 | Chucholowski et al. | |
| 2010/0093662 A1 | 4/2010 | Defaye et al. | |

FOREIGN PATENT DOCUMENTS

| | | |
|---|---|---|
| DE | 10 2010 012 281 A1 | 9/2011 |
| FR | 2 852 959 A1 | 10/2004 |
| JP | 2002535440 A | 10/2002 |
| WO | 2008/009831 A2 | 1/2008 |
| WO | 2010/127600 A1 | 11/2010 |
| WO | 2013/123254 A2 | 8/2013 |

OTHER PUBLICATIONS

Adam, M. J. et al., "Cyclodextrin-Derived Host Molecules as Reveral Agents for the Neuromuscular Blocker Rocuronium Bromide: Syntesis and Structure-Activity Relationships" J. Med. Chem. (2002); vol. 45; pp. 1806-1816.
Garcia-Barrientos, J. J. et al., "Synthesis of β-Cyclodextrin, per-O-glycosylated through an Ethylene Glycol Spacer Arm", Synthesis (2001); Paper No. 7; pp. 1057-1064.
Nelles, G. et al., "Controlled Orientation of Cyclodextrin Derivatives Immoblized on Gold Surfaces", J. Am. Chem. Soc. (1996); vol. 118; pp. 5039-5046.
Qian, J. et al., "Superstructures of Cyclodextrin Derivatives on Au(I111): A Combined Random Planting-Molecular Dynamics Approach", Langmuir (1997); vol. 13; pp. 7092-7098.
Sauer, J. et al., "Stability and Function of Interdomain Linker Variants of Glycoamylase 1 from Aspergillus niger"; Biochem (2001); vol. 40; pp. 9336-9346.
Sigurskjold, B. W. et al., "Thermodynamics of Binding of Heterobidentate Ligands Consisting of Spacer-Connected Acarbose and β-Cyclodextrin to the Catalytic and Starch-Binding Domains of Glucoamylase from Aspergillus niger Shows that the Catalytic and Starch-Binding Sites are in Close Proximity in Space", Biochem. (1998); vol. 37; pp. 10446-10452.
Wang H. M. et al., "Topochemical Control of the Photodimerization of Aromatic Compounds by Y-Cyclodextrin Thioethers in Aqueous Solution", Bielstein J. of Org. Chem. (2013); vol. 9; pp. 1858-1866.
Zhong, N. et al., "Selective Removal of Palmitic Acid from Langmuir Monolayers by Complexation with New Quatemary Ammonium β-Cyclodextrin Derivaives" Langmuir (2001); vol. 17; pp. 5319-5323.
ACS Publications, Bioconjugate Chemistry, 2003, vol. 14(5), p. 899-908.
Journal of the American Chemical Society, 2007, vol. 129(20), p. 6396-6397.
Macromolecules, 2007, vol. 40(9), p. 3256-3262.
Journal of the American Chemical Society, 2006, vol. 128(28), p. 8994-8995.
Journal of Colloid and Interface Science, 2004, vol. 279(2), p. 425-432.
Journal of Polymer Science, Part A: Polymer Chemistry 2007, vol. 45(22), p. 5149-5155.

*Primary Examiner* — Po-Chih Chen
(74) *Attorney, Agent, or Firm* — Bennett Jones LLP

(57) ABSTRACT

The present application provides polyanionic and non-ionic cyclodextrin-based compounds, and methods of manufacturing them. The compounds comprise a negatively-charged or neutral moiety (and, for polyanionic compounds, a suitable counter cation), one or more linkers, optionally one or more bridging groups, a cyclodextrin, and one or more substituents on the cyclodextrin. The compounds can be used in pharmaceutical compositions, and as excipients or carriers of guest molecules.

6 Claims, 19 Drawing Sheets

R = –G-L-X⁻ Y⁺ (such as -S-G-L-X⁻ Y⁺) or –OH.

R = –G-L-X' (such as -S-G-L-X') or –OH.

CYCLODEXTRIN-BASED POLYANIONIC AND NON-IONIC DENDRIMERS

FIELD

The present application pertains to the field of cyclodextrins. More particularly, the present application relates to cyclodextrin-based polyanionic and non-ionic dendrimers for use in pharmaceutical applications.

BACKGROUND

Cyclodextrins (CDs) are a class of non-toxic, water-soluble D-glucose based macrocycles with a hydrophobic cavity. CDs typically vary by the number of glucose units. Common members include α-CD (6 glucose units), β-CD (7 glucose units) and γ-CD (8 glucose units), with increasing cavity size. The varying cavity sizes offer increased utility in a wide variety of applications, particularly in drug delivery models. For example, CDs can be used to form "inclusion complexes" in which a drug is included and carried within the cavity. This can be used as a pharmaceutical excipient to improve drug water solubility, chemical stability, and removal of certain drug side effects (such as undesirable taste). CDs have also drawn interest in the cosmetic and food additives industries, in the design of artificial enzymes, gene delivery vehicles, sensors and novel supramolecular assemblies.

CDs can be native or chemically modified on either or both of their primary and/or secondary faces. Typically, an inclusion complex often has lower water solubility than native CDs. Chemical modifications of CDs can change their physico-chemical properties. For example, adding a tosyl group on the primary face of the β-CD renders the molecule near insoluble at room temperature, while adding methyl groups at OH-6 and OH-2 positions significantly increases water solubility. The toxicity of the molecule can also be changed. Therefore, modification of the CD molecule may present certain advantages. However, chemical modification of CDs is typically difficult to achieve, often leading to the formation of a mixture of products that are difficult to separate.

The groups added to the primary or second face can be neutral or charged. For example, Captisol® is an excipient for use with a number of drugs. It is a polyanionic mixture of β-CD derivative having from 1 to 10 sodium sulfobutyl ether groups directly attached via oxygen atoms of the D-glucose thereto (U.S. Pat. No. 5,134,127 (Stella et al)). Capitsol is prepared by reacting a β-CD with 1,4-butyl sultone and sodium hydroxide in water. The obtained product is a mixture containing many positional and regioisomers with varying degrees of substitution at different oxygen positions on the CD, such as substitution at O-2, O-3 and O-6 on the CD. (Luna, et al., *Carbohydr. Res.,* 299, 103-110, 1997; Luna, et al., *Carbohydr. Res.,* 299, 111-118, 1997; Rogmann et al., *Carbohydr. Res.,* 327, 275-285, 2000; http://www.captisol.com/faq/solution-and-solid-state-characteristics-in-captisol).

There are certain disadvantages with Captisol. As it comprises a mixture of compounds, thus resulting in varied compositions, it is difficult if not impossible to define and characterize the product compositions.

Another polyanionic CD compound currently on the market is Sugammadex (by Merck), which is a polyanionic agent obtained from γ-CD. Sugammadex blocks the activity of neuromuscular agents (Yan, et al., *Drugs,* 2009: 69, 919-42; Calderón-Acedos, et al. *Eur. J. Hosp. Pharm.* 2012: 19, 248). See also U.S. Pat. No. 6,670,340 (Zhang et al.) and U.S. Pat. No. 6,949,527 (Zhang et al.).

Non-ionic CD-based compounds are also known in the art. One example includes hydroxypropyl-beta CD (HPBCD). However, this exists in a mixture of compounds, similarly resulting in varied compositions.

There is a need for pure anionic or non-ionic CD derivatives for various applications in the pharmaceutical industry, such as those described herein, for example.

This background information is provided for the purpose of making known information believed by the applicant to be of possible relevance to the present invention. No admission is necessarily intended, nor should be construed, that any of the preceding information constitutes prior art against the present invention.

SUMMARY

An object of the present invention is to provide improved pure polyanionic and non-ionic cyclodextrin-based compounds, which can be used in various pharmaceutical related applications.

In accordance with an aspect of the present invention, there is provided a polyanionic cyclodextrin-based compound of the formula $$Y^{(+)}X^{(-)}\text{-L-G-D-R} \qquad \text{(Formula I)}$$

wherein $X^{(-)}$ is one or more negatively charged moieties, $Y^{(+)}$ is one or more counter cations, L is one or more linkers, G is a bond or is one or more bridging groups, D is a cyclodextrin, and R is one or more substituents.

The charged moiety $X^{(-)}$ can be any suitable negatively charged moiety. Non-limiting examples include $—SO_3^-$, $—CO_2^-$, $—OSO_3^-$, $—OPO_3^-$, for example.

The linker L can comprise a substituted or unsubstituted alkyl group (such as a $C_1$-$C_{11}$ alkyl group, for example), and/or a substituted or unsubstituted polyethylene glycol (PEG) group, or a combination of one or more alkyl groups and one or more PEG groups. In an exemplary embodiment, the PEG group is of the formula $—CHZ(CH_2OCHZ)_mCH_2—$ where Z is H or $CH_3$ and m is 1 to 20, for example; however, any suitable PEG group, if present, may be contemplated. In certain embodiments, L can comprise any unsubstituted or substituted alkyl group; for example, the alkyl group may be substituted with a PEG group. However, any suitable substituent may be contemplated. In other embodiments, L can comprise an unsubstituted or substituted PEG group; for example, the PEG group may be substituted with one or more alkyl groups. However, any suitable substituent may be contemplated. In certain other embodiments, L comprises a PEG group which has none, or one or more alkyl groups flanking on either or both sides of the PEG group. One or more of the $CH_2$ groups of the alkyl group may be replaced with an atom or functional group. Non-limiting examples of the atom or functional group include $—O—$, $—S—$, $—SO—$, $—SO_2—$, $—CONH—$, $—COO—$, $—NZ—$, or a substituted or unsubstituted 1,2,3-triazole group, for example. Examples of substituted 1,2,3-triazole groups may include those substituted with a group comprising one of the following structures:

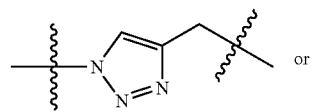

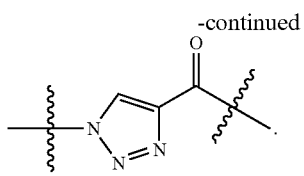

The cyclodextrin D can comprise, for example, 6, 7, or 8 glucose subunits, typically 7.

In certain embodiments, G represents any one or more suitable bridging groups. G may represent, for example, an ester, amide, amine, sulfur, or a substituted or unsubstituted 1,2,3-triazole. Non-limiting examples of bridging groups for G include —S—, —OC(O)—, —NHC(O)—, —SO—, —SO₂—, or a substituted or unsubstituted 1,2,3-triazole group. Examples of substituted 1,2,3-triazole groups may include those substituted with a group comprising one of the following structures:

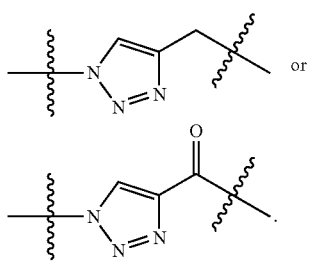

However, other suitable bridging groups may be contemplated. In certain other embodiments, G is a bond.

The substituent R can be any one or more suitable substituents. Non-limiting examples include H, an optionally substituted alkyl group or an optionally substituted acyl group. In certain embodiments, the optionally substituted alkyl group or acyl group is a $C_1$-$C_{18}$ group, for example.

$Y^{(+)}$ can be any pharmaceutically acceptable cation, typically $Na^+$ or $K^+$, for example.

In certain embodiments, the polyanionic cyclodextrin (CD)-based compound is:

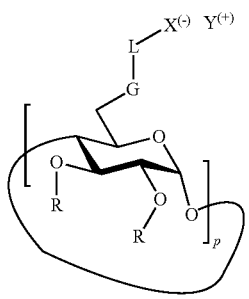

(II)

where R, L, G, $X^{(-)}$ and $Y^{(+)}$ are defined above and wherein the cyclodextrin subunit is shown where p is 6, 7 or 8, typically 7.

In accordance with another aspect there is provided a non-ionic cyclodextrin-based compound of the formula

 X'-L-G-D-R  (Formula III)

wherein X' is one or more neutral moieties; L is one or more linkers; G is a bond or is one or more bridging groups; D is a cyclodextrin; and R is one or more substituents.

Examples of X' may include, for example, an unsubstituted or substituted amide including its N-substituted forms (such as —CONH₂, for example), a nitrile group (—CN), or a polyhydroxylated residue (such as a carbohydrate for example).

The linker L can comprise a substituted or unsubstituted alkyl group (such as a $C_1$-$C_{11}$ alkyl group, for example), and/or a substituted or unsubstituted polyethylene glycol (PEG) group, or a combination of one or more alkyl groups and one or more PEG groups. In an exemplary embodiment, the PEG group is of the formula —CHZ(CH₂OCHZ)$_m$CH₂— where Z is H or CH₃ and m is 1 to 20, for example; however, any suitable PEG group, if present, may be contemplated. In certain embodiments, L can comprise any unsubstituted or substituted alkyl group; for example, the alkyl group may be substituted with a PEG group. However, any suitable substituent may be contemplated. In other embodiments, L can comprise an unsubstituted or substituted PEG group; for example, the PEG group may be substituted with one or more alkyl groups. However, any suitable substituent may be contemplated. In certain other embodiments, L comprises a PEG group which has none, or one or more alkyl groups flanking on either or both sides of the PEG group. One or more of the CH₂ groups of the alkyl group may be replaced with an atom or functional group. Non-limiting examples of the atom or functional group include —O—, —S—, —SO—, —SO₂—, —CONH—, —COO—, —NZ—, or a substituted or unsubstituted 1,2,3-triazole. Examples of substituted 1,2,3-triazole groups may include those substituted with a group comprising one of the following structures:

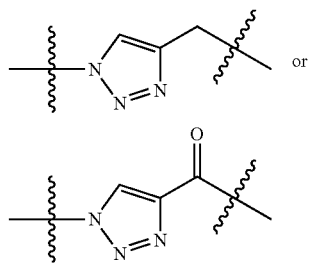

for example.

The cyclodextrin D can comprise, for example, 6, 7, or 8 glucose subunits, typically 7.

In certain embodiments, G represents any one or more suitable bridging groups. G may represent, for example, an ester, amide, amine, sulfur, or a substituted or unsubstituted 1,2,3-triazole. Non-limiting examples of bridging groups for G include —S—, —OC(O)—, —NHC(O)—, —SO—, —SO₂—, or a substituted or unsubstituted 1,2,3-triazole group. Examples of substituted 1,2,3-triazole groups may include those substituted with a group comprising one of the following structures

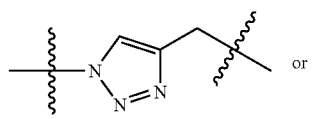

-continued

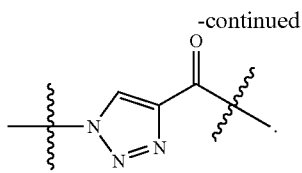

However, other suitable bridging groups may be contemplated. In certain other embodiments, G is a bond.

The substituent R can be any one or more suitable substituents. Non-limiting examples include H, an optionally substituted alkyl group or an optionally substituted acyl group. In certain embodiments, the optionally substituted alkyl group or acyl group is a $C_1$-$C_{18}$ group, for example.

In certain embodiments, the non-ionic CD-based compound is:

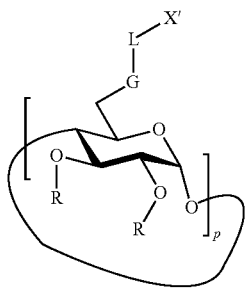

(Formula IV)

where R, L, G and X' are as defined above and wherein the cyclodextrin subunit D is shown where p is 6, 7 or 8, typically 7.

In certain embodiments, the present application provides a polyanionic cyclodextrin-based compound as described herein, wherein p is 6 (α-cyclodextrin), 7 (β-cyclodextrin) or 8 (γ-cyclodextrin), $X^{(-)}$ is —$CO_2^-$ or —$SO_3^-$; G is —S—; L is —$(CH_2)_k$—, where k is 1 to 11, optionally 7 to 11; or L is

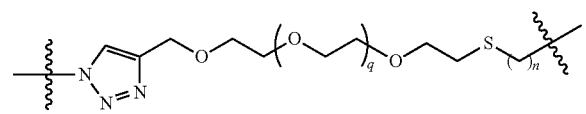

where q is 0 to 20 and n is 1-5, optionally 1-11, or

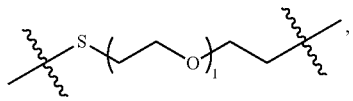

where l is 1-20; and R is H, optionally substituted $C_1$-$C_{18}$ alkyl, or optionally substituted $C_1$-$C_{18}$ acyl.

The present application also provides a method of synthesizing the polyanionic or non-ionic cyclodextrin-based compounds, substantially as described herein.

In one aspect, there is provided a method of synthesizing a polyanionic compound as described herein, comprising reacting alkyl sultones of the formula:

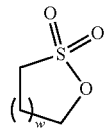

(Formula V)

with a salt of thioacetate ($AcS^-M^+$) where $M^+$ is a counter cation such as $Na^+$ or $K^+$, which generates a compound of the formula:

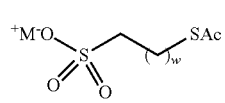

(Formula VI)

as a reagent to react with a compound of the formula:

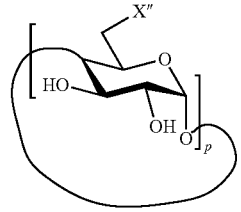

(Formula VII)

where X" is a halide such as Cl, Br, or I, p is 6 to 8, in an alcohol solvent (such as methanol, for example) together with a polar solvent (such as DMSO, for example), using a base (such as an alkoxide, for example) to obtain a polyanionic cyclodextrin-based compound. In certain embodiments, L is —$(CH_2)_w$—, where w is 1 to 3; R is H; and G is —S—.

The compounds as described herein can be used in various pharmaceutical applications, such as excipients or by inclusion with other molecules. In one example, a cyclodextrin as described herein can be included with cholic acid.

BRIEF DESCRIPTION OF THE FIGURES

For a better understanding of the present invention, as well as other aspects and further features thereof, reference is made to the following description which is to be used in conjunction with the accompanying drawings, where.

DETAILED DESCRIPTION

Figure 1:
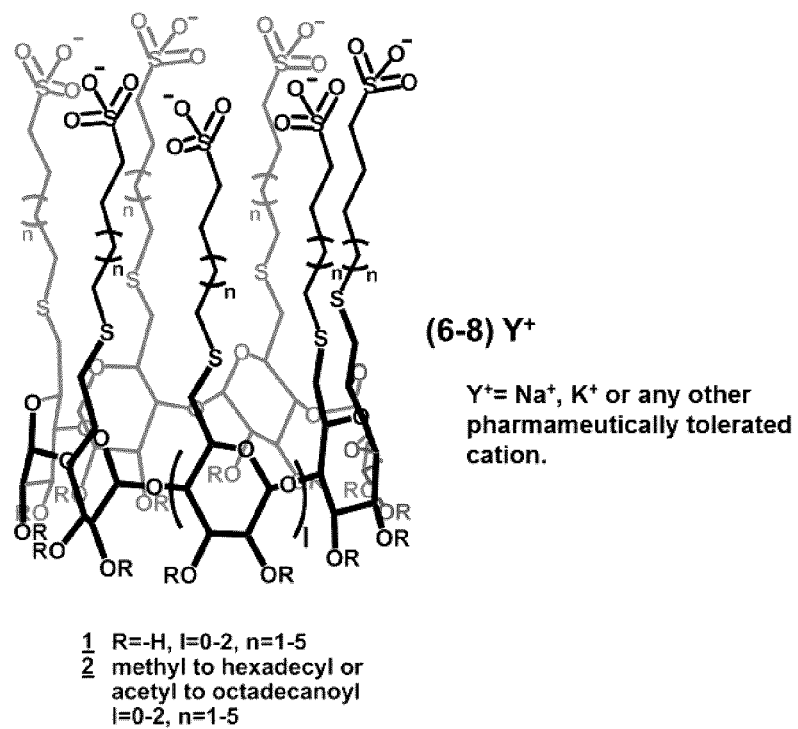
FIG. 1 shows an exemplary representation of thioether-linked sulfoalkyl polyanionic CD-based compounds.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, the term "aliphatic" refers to a linear, branched or cyclic, saturated or unsaturated non-aromatic hydrocarbon. Examples of aliphatic hydrocarbons include alkyl groups.

As used herein, the term "alkyl" refers to a linear, branched or cyclic, saturated or unsaturated hydrocarbon group which can be unsubstituted or is optionally substituted with one or more substituent. Examples of saturated straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl and 2-ethyl-1-butyl, 1-heptyl and 1-octyl. As used herein the term "alkyl" encompasses cyclic alkyls, or cycloalkyl groups. The term "cycloalkyl" as used herein refers to a non-aromatic, saturated monocyclic, bicyclic or tricyclic hydrocarbon ring system containing at least 3 carbon atoms. Examples of $C_3$-$C_{12}$ cycloalkyl groups include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl. Chemical functional groups, such as ether, thioether, sulfoxide, or amine, amide, ammonium, ester, phenyl, 1,2,3-triazole etc can be incorporated alkyl group to help extend the length of the chain.

As used herein, the term "substituted" refers to the structure having one or more substituents. A substituent is an atom or group of bonded atoms that can be considered to have replaced one or more hydrogen atoms attached to a parent molecular entity. Examples of substituents include aliphatic groups, halogen, arylcarbonyloxy, alkoxycarbonyloxy, aryloxycarbonyloxy, alkoxycarbonyl, aminocarbonyl, alkylthiocarbonyl, alkoxyl, phosphate ester, phosphonato, phosphinato, cyano, tertiary amino, tertiary acylamino, tertiary amide, imino, alkylthio, arylthio, sulfonato, sulfamoyl, tertiary sulfonamido, nitrile, trifluoromethyl, heterocyclyl, aromatic, and heteroaromatic moieties, ether, ester, boron-containing moieties, tertiary phosphines, and silicon-containing moieties.

As used herein, the term "hydrophilic" refers to the physical property of a molecule or chemical entity or substituent within a molecule that tends to be miscible with and/or dissolved by water, or selectively interacts with water molecules. Hydrophilic groups can include polar groups. By contrast, as used herein, the term "hydrophobic" refers to the physical property of a molecule or chemical entity or substituent within a molecule that tends to be immiscible with and/or insoluble in water, or selectively repels water molecules.

As used herein, the term "amphiphilic" refers to the physical property of a molecule or chemical entity that possesses both hydrophilic and hydrophobic properties.

As used herein, the term "anionic" refers to a negatively charged molecule or part thereof which imparts the negative charge.

In the present document, the hydrophobic groups are illustrated to be placed at the secondary face of a CD while the hydrophilic groups are placed at the primary face of a CD. These two groups can be swapped to link to the opposite face of a CD.

The present application provides polyanionic and non-ionic CD-based compounds, ideally in a pure form.

The present application also provides a pharmaceutical composition comprising a medicament and a polyanionic or non-ionic CD-based compound as described herein. The present application also provides the polyanionic or non-ionic compound as described herein as an excipient and/or as carriers of guest molecules.

Ideally, the polyanionic and non-ionic CD-based compounds as described herein can use thioether or its oxidized form (sulfone or sulfoxide) as the linking group instead of ether as done previously in the art. This results in structurally well-defined polyanionic and non-ionic CD-based compounds in pure form that are easier to characterize. As such, the polyanionic and non-ionic CD-based compounds of the present application are suitable for generating drug formulations in well-defined compositions.

Advantageously, the present polyanionic and non-ionic CD-based compounds can bind to other molecules with better affinity due to the symmetric nature of the cavity within the CD. The cavity can accommodate larger or smaller molecules as the polyanionic or non-ionic CD can be an α, β, or γ analog.

The polyanionic and non-ionic CD-based compounds can be designed to be either totally water-soluble (with short chains, where R is H, methyl to n-propyl, or acetyl to n-propanoyl) or self-assemble (with longer chains, where R is n-butyl to n-octadecyl or n-butanoyl to n-octadecanoyl) to form nanoparticles (micelles) in water. These structures ideally bind to hydrophobic drug molecules with better affinities because of the alkyl chains and the PEG linker groups.

Polyanionic CD-Based Compounds

In accordance with one aspect, there is provided a polyanionic cyclodextrin-based compound of the formula $$Y^{(+)}X^{(-)}\text{-L-G-D-R} \quad \text{(Formula I)}$$

wherein $X^{(-)}$ is one or more negatively charged moieties, $Y^{(+)}$ is one or more counter cations, L is one or more linkers, G is a bond or is one or more bridging groups, D is a cyclodextrin, and R is one or more substituents.

The charged moiety $X^{(-)}$ can be any suitable negatively charged moiety. Non-limiting examples include $-SO_3^-$, $-CO_2^-$, $-OSO_3^-$, $-OPO_3^-$, for example.

The linker L can comprise a substituted or unsubstituted alkyl group (such as a $C_1$-$C_{11}$ alkyl group, for example), and/or a substituted or unsubstituted polyethylene glycol (PEG) group, or a combination of one or more alkyl groups and one or more PEG groups. In an exemplary embodiment, the PEG group is of the formula $-CHZ(CH_2OCHZ)_mCH_2-$ where Z is H or $CH_3$ and m is 1 to 20, for example; however, any suitable PEG group, if present, may be contemplated. In certain embodiments, L can comprise any unsubstituted or substituted alkyl group; for example, the alkyl group may be substituted with a PEG group. However, any suitable substituent may be contemplated. In other embodiments, L can comprise an unsubstituted or substituted PEG group; for example, the PEG group may be substituted with one or more alkyl groups. However, any suitable substituent may be contemplated. In certain other embodiments, L comprises a PEG group which has none, or one or more alkyl groups flanking on either or both sides of the PEG group. One or more of the $CH_2$ groups of the alkyl group may be replaced with an atom or functional group. Non-limiting examples of the atom or functional group include $-O-$, $-S-$, $-SO-$, $-SO_2-$, $-CONH-$, $-COO-$, $-NZ-$, or a substituted or unsubstituted 1,2,3-triazole group, for example. Examples of substituted 1,2,3-triazole groups may include those substituted with a group comprising one of the following structures:

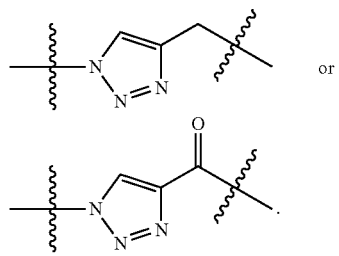

The cyclodextrin D can comprise, for example, 6, 7, or 8 glucose subunits, typically 7.

In certain embodiments, G represents any one or more suitable bridging groups. G may represent, for example, an ester, amide, amine, sulfur, or a substituted or unsubstituted 1,2,3-triazole. Non-limiting examples of bridging groups for G include $-S-$, $-OC(O)-$, $-NHC(O)-$, $-SO-$, $-SO_2-$, or a substituted or unsubstituted 1,2,3-triazole group. Examples of substituted 1,2,3-triazole groups may include those substituted with a group comprising one of the following structures:

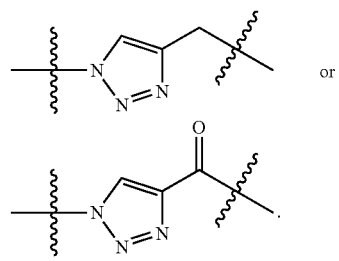

However, other suitable bridging groups may be contemplated. In certain other embodiments, G is a bond.

The substituent R can be any one or more suitable substituents. Non-limiting examples include H, an optionally substituted alkyl group or an optionally substituted acyl group. In certain embodiments, the optionally substituted alkyl group or acyl group is a $C_1$-$C_{18}$ group, for example.

$Y^{(+)}$ can be any pharmaceutically acceptable cation, typically $Na^+$ or $K^+$, for example.

In certain embodiments, the polyanionic cyclodextrin (CD)-based compound is:

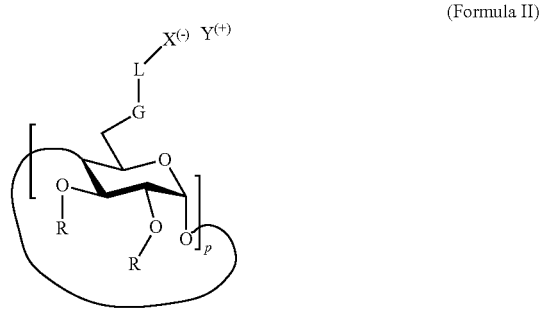

(Formula II)

where R, L, G, $X^{(+)}$ and $Y^{(+)}$ are defined herein and wherein the cyclodextrin subunit is shown where p is 6 to 8, typically 7.

The number of linkers attached to the cyclodextrin can vary but are typically the same length within a given CD-based molecule.

The CD core (i.e., D) comprises any number of glucose subunits. In certain embodiments, there are 6, 7, or 8 glucose subunits, typically 7. Therefore, in certain embodiments, a β-CD is contemplated.

On the secondary face of the CD are attached one or more, typically a plurality of substituents, R. The substituents can be H, an alkyl or acyl group. In certain embodiments, the chains are bonded to either O2 or O3 of the CD group, or both O2 and O3 groups. The length of the group can vary from $C_1$-$C_{18}$, for example.

Non-Ionic CD-Based Compounds

In accordance with another aspect, there is provided a non-ionic cyclodextrin-based compound of the formula $$X'\text{-L-G-D-R} \quad \text{(Formula III)}$$

wherein X' is one or more neutral moieties; L is one or more linkers; G is a bond or is one or more bridging groups; D is a cyclodextrin; and R is one or more substituents.

Examples of X' may include, for example, an unsubstituted or substituted amide including its N-substituted forms (such as $-CONH_2$, for example), a nitrile group ($-CN$), or a polyhydroxylated residue (such as a carbohydrate for example).

The linker L can comprise a substituted or unsubstituted alkyl group (such as a $C_1$-$C_{11}$ alkyl group, for example), and/or a substituted or unsubstituted polyethylene glycol (PEG) group, or a combination of one or more alkyl groups and one or more PEG groups. In an exemplary embodiment, the PEG group is of the formula —CHZ(CH$_2$OCHZ)$_m$CH$_2$— where Z is H or CH$_3$ and m is 1 to 20, for example; however, any suitable PEG group, if present, may be contemplated. In certain embodiments, L can comprise any unsubstituted or substituted alkyl group; for example, the alkyl group may be substituted with a PEG group. However, any suitable substituent may be contemplated. In other embodiments, L can comprise an unsubstituted or substituted PEG group; for example, the PEG group may be substituted with one or more alkyl groups. However, any suitable substituent may be contemplated. In certain other embodiments, L comprises a PEG group which has none, or one or more alkyl groups flanking on either or both sides of the PEG group. One or more of the CH$_2$ groups of the alkyl group may be replaced with an atom or functional group. Non-limiting examples of the atom or functional group include —O—, —S—, —SO—, —SO$_2$—, —CONH—, —COO—, —NZ—, or a substituted or unsubstituted 1,2,3-triazole. Examples of substituted 1,2,3-triazole groups may include those substituted with a group comprising one of the following structures:

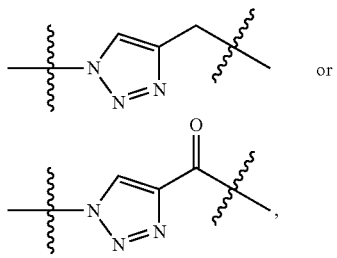

for example.

The cyclodextrin D can comprise, for example, 6, 7, or 8 glucose subunits, typically 7.

In certain embodiments, G represents any one or more suitable bridging groups. G may represent, for example, an ester, amide, amine, sulfur, or a substituted or unsubstituted 1,2,3-triazole. Non-limiting examples of bridging groups for G include —S—, —OC(O)—, —NHC(O)—, —SO—, —SO$_2$—, or a substituted or unsubstituted 1,2,3-triazole group. Examples of substituted 1,2,3-triazole groups may include those substituted with a group comprising one of the following structures:

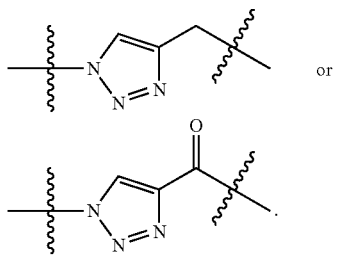

However, other suitable bridging groups may be contemplated. In certain other embodiments, G is a bond.

The substituent R can be any one or more suitable substituents. Non-limiting examples include H, an optionally substituted alkyl group or an optionally substituted acyl group. In certain embodiments, the optionally substituted alkyl group or acyl group is a $C_1$-$C_{18}$ group, for example.

In certain embodiments, the non-ionic CD-based compound is:

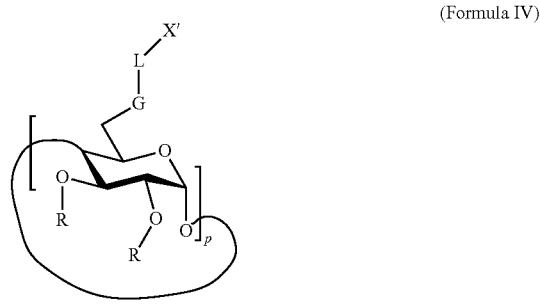

(Formula IV)

where R, L, G and X' are defined above and wherein the cyclodextrin subunit is shown where p is 6 to 8, typically 7.

The number of alkyl and/or PEG groups can vary but are typically the same length within a given CD-based molecule.

EXAMPLES

Example 1: Polyanionic CD-Based Compounds and Synthesis Thereof

FIG. 1 shows an exemplary thioether-linked sulfoalkyl polyanionic CD-based compound. The molecule comprises a saturation of the CD groups with butyl (tetramethylene) as the linker and thioether as the bridging functionality to connect the linkers to cyclodextrin. The length of the linker can vary. Exemplary R groups on the secondary face of the CD are shown.

Figure 2:
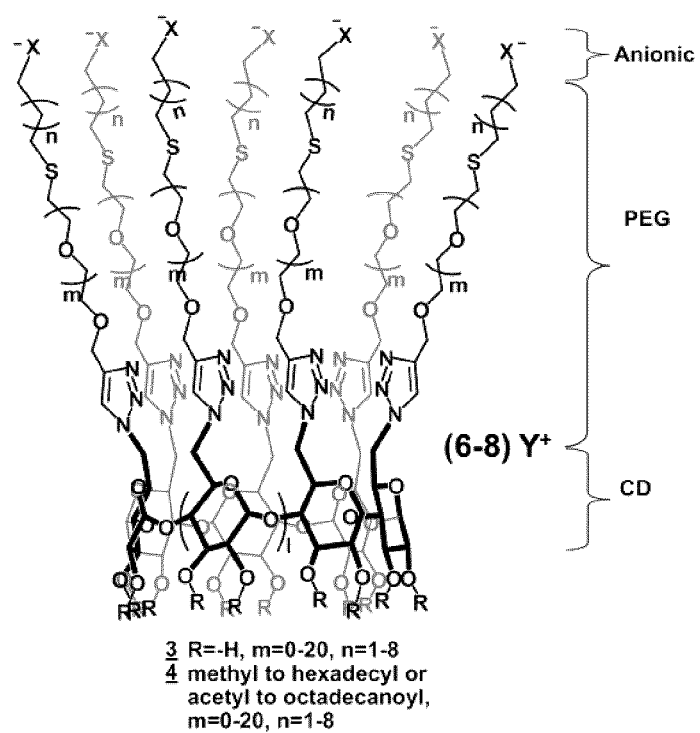
FIG. 2 shows another exemplary representation of thioether-linked polyanionic CDs with an additional PEG-ylated linker group.

FIG. 2 shows an exemplary polyanionic CD with a PEG-ylated linker group. As shown, the anionic group can be any suitable group, such as —SO$_3^-$ or —CO$_2^-$ for example. The PEG segment can include 1 to 20 repeating ethylene glycol groups. Typically, the bridging group used to connect PEG segment to D-glucose is a substituted 1,2,3-triazole group such as the (1,2,3-triazole-4-yl)methyl or (1,2,3-triazole-4-yl)carbonyl group. The compound can be either a water-soluble polyionic cyclodextrin (R=H, methyl to n-butyl) or capable of self-assembling in water (R=longer than n-butyl). Y$^+$ can be Na$^+$, K$^+$ or any other pharmaceutically tolerated cation.

Figure 3:
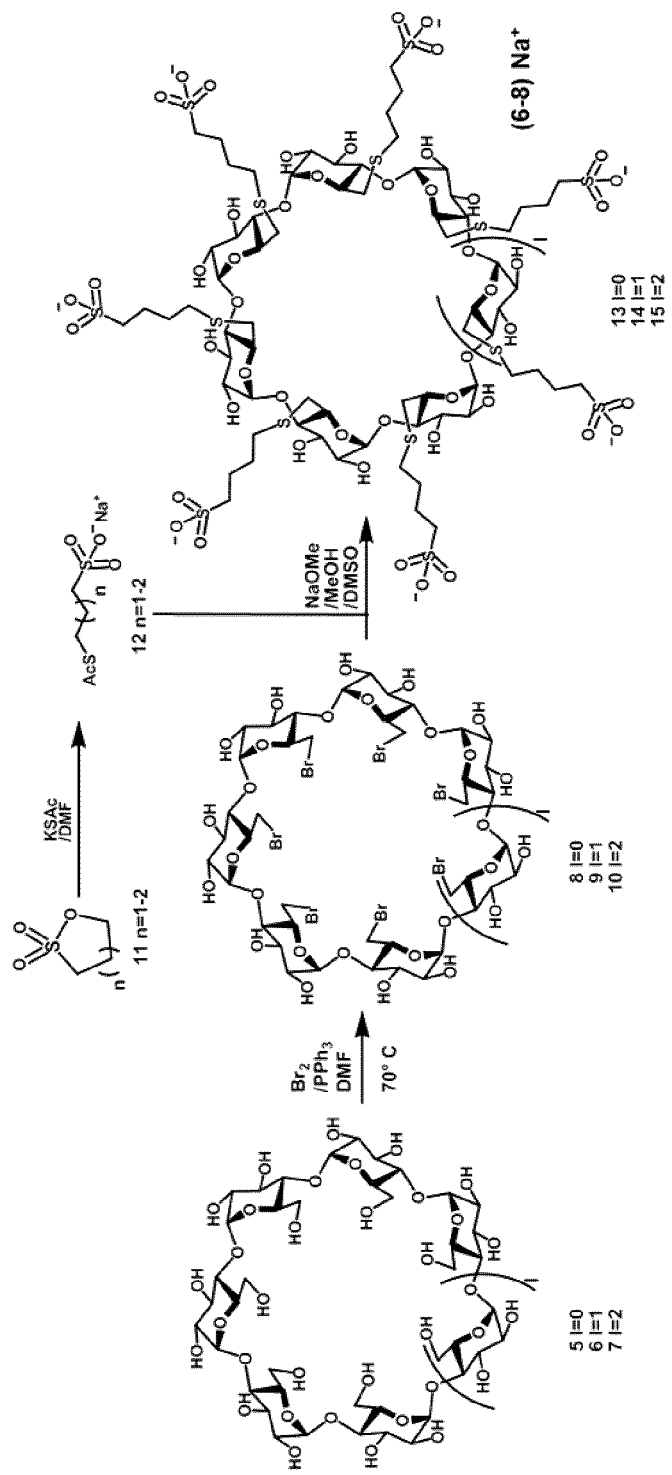
FIG. 3 shows an exemplary synthesis of thioether-linked sulfoalkyl polyanionic CDs.

FIG. 3 shows an exemplary synthesis for polyanionic CD containing sulfoalkyl group via thioether linkage. As shown, the anionic group can be any suitable group, such as —SO$_3^-$ for example. The leaving group on the cyclodextrin is shown to be bromide, but may also be another conventional halide such as chloride or iodide.

Figure 4:
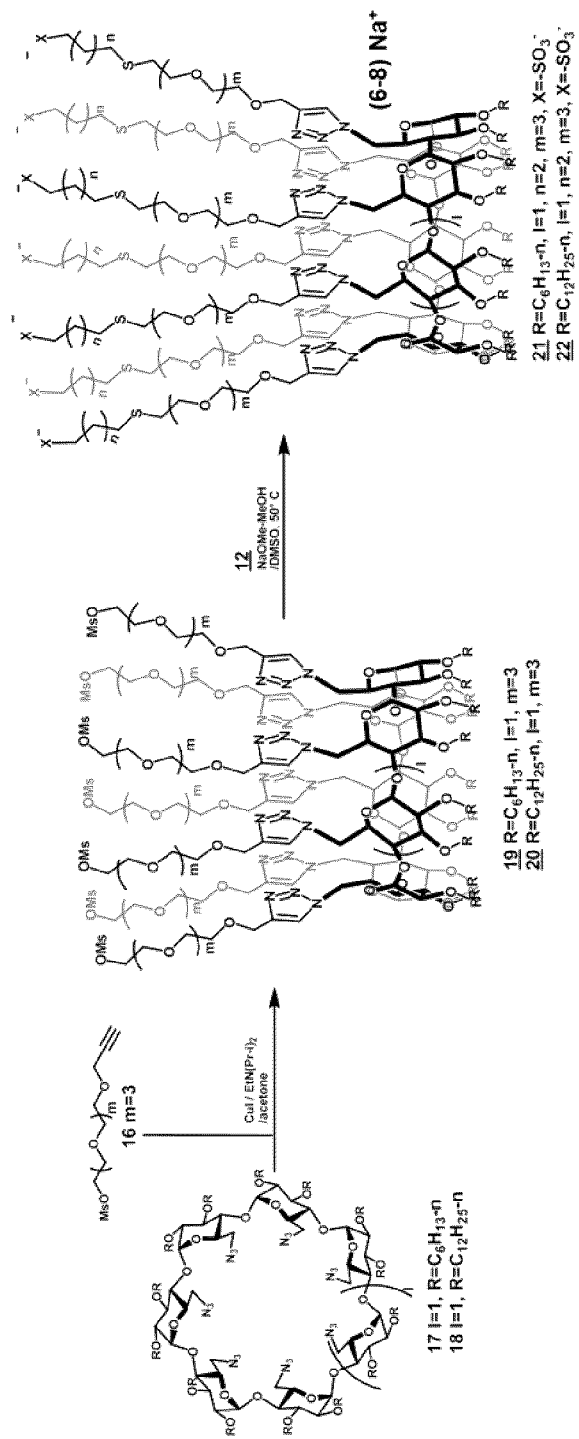
FIG. 4 shows an exemplary synthesis of thioether-linked sulfoalkyl analogs.

FIG. 4 shows an exemplary synthesis of an amphiphilic sulfoakyl thioether analog. Ideally, the synthesis requires as little as two steps from a known 2,3-alkylated or acylated CD compound such as compounds 17 or 18. Copper(I)-mediated 1,3-dipolar cycloaddition permits the efficient synthesis of mesylates 19 and 20 from an alkyne-functionalized PEG derivative (16). A highly nucleophilic thiolate containing sulfoalkyl group, generated in situ from the thioacetate precursor, is used to react with the mesylated CD compound to form CDs comprising thioether-linked sulfoalkyls (21, 22).

Figure 5:
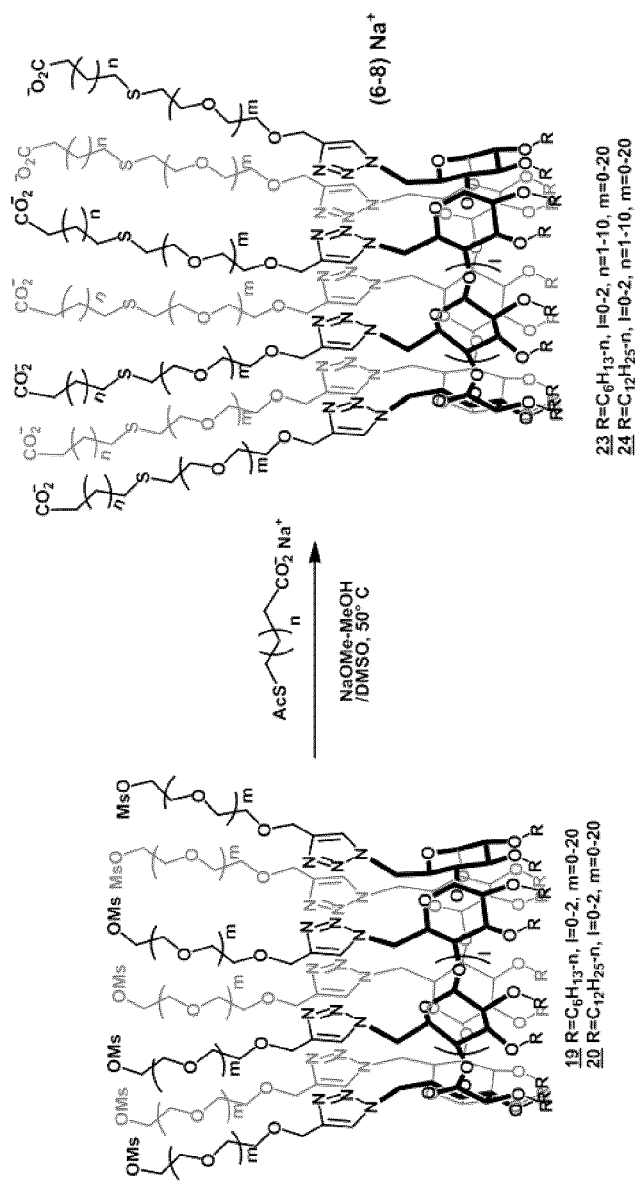
FIG. 5 shows an exemplary synthesis of thioether-linked carboxyalkyl analogs.

FIG. 5 shows an exemplary synthesis of a carboxyalkyl thioether analog. A mesylated CD starting material (19, 20) is reacted with an S-thioacetyl-functionalized carboxylic acid to form the carboxyalkyl-functionalized CDs via thioether group (23, 24).

Example 2: Polyanionic SulfoPEG Thioether Cyclodextrins

Figure 6:
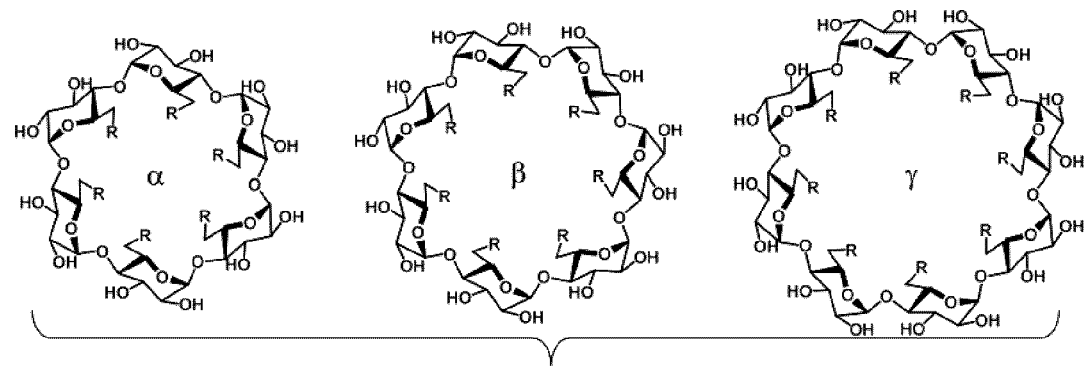
FIG. 6 shows exemplary polyanionic sulfoPEG thioether cyclodextrins.

FIG. 6 shows α, β and γ embodiments of CDs as described herein. In these embodiments, the 6-hydroxyl groups of native cyclodextrins are partially or completely replaced with R groups of the formula -G-L-X$^-$Y$^+$, —S-G-L-X$^-$Y$^+$ or —OH. G, L, X and Y are as defined above.

Figure 7:
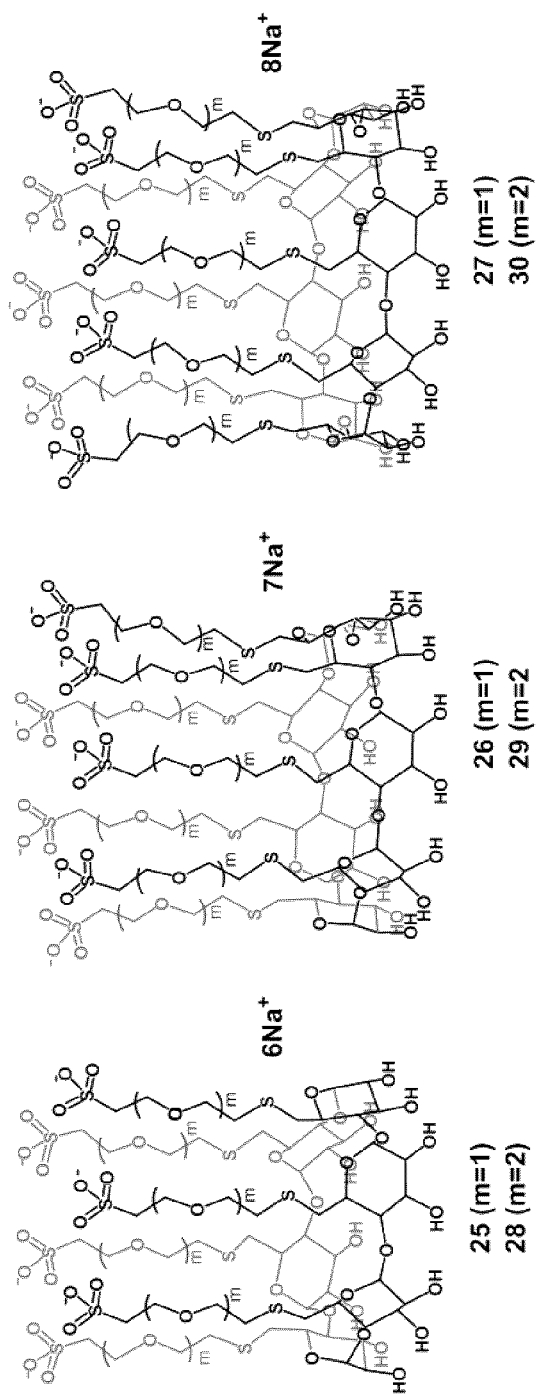
FIG. 7 shows exemplary sulfoPEG thioether cyclodextrin analogs.

FIG. 7 shows examples of synthesized sulfoPEG thioether CD analogs (25-30). Left panel shows two α-CD derivatives (25 and 28) containing different length of linker, middle panel shows two β-CD analogs (26 and 29) and right panel show two γ-CD analogs (27 and 30). In each pair of example shown, the number of PEG group varies between two and three units; however, it may be contemplated as stated above that any number of PEG groups may be present.

Figure 8:
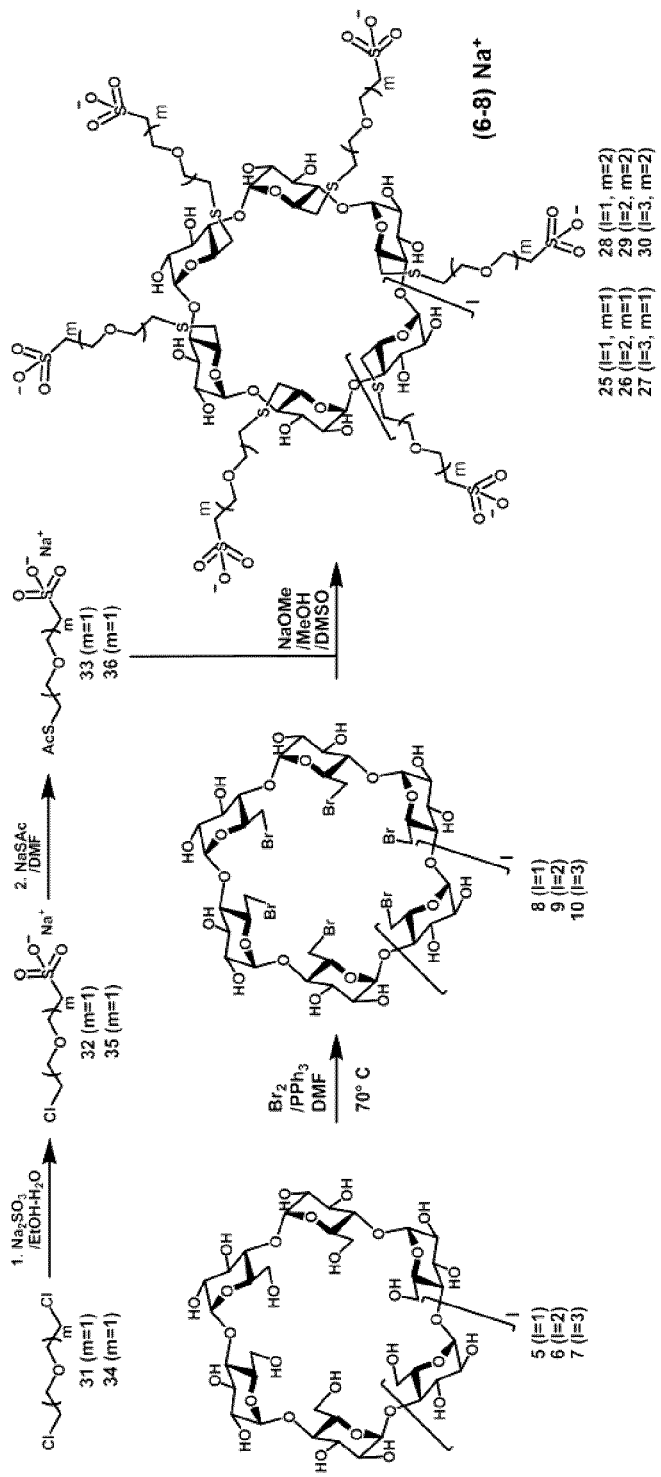
FIG. 8 shows an exemplary synthesis of sulfoalkyl thioether analogs.

FIG. 8 shows an exemplary synthesis of sulfoPEG thioether analogs as described herein. Typically, an α,ω-dichloride of a PEG of any length (31, 34) is reacted with sodium sulfite to selectively replace one of the chlorides with the sulfonate. The remaining chloride (32, 35) is then substituted with thioacetate. The obtained reagent (33, 36) is then reacted with a cyclodextrin derivative (8-10, derived from 5-7) bearing leaving group(s) (Br) at the primary carbon (C6) under basic condition in an alcohol-dimethyl sulfoxide (DMSO) mixture; the reaction generates a reactive thiolate intermediate from the reagent that attacks the cyclodextrin substrate to provide the anionic cyclodextrin product. Here the per-6-substituted derivatives (25-30) were prepared and obtained in pure form.

Example 3: Non-Ionic CD-Based Compounds and Synthesis Thereof

Figure 9:
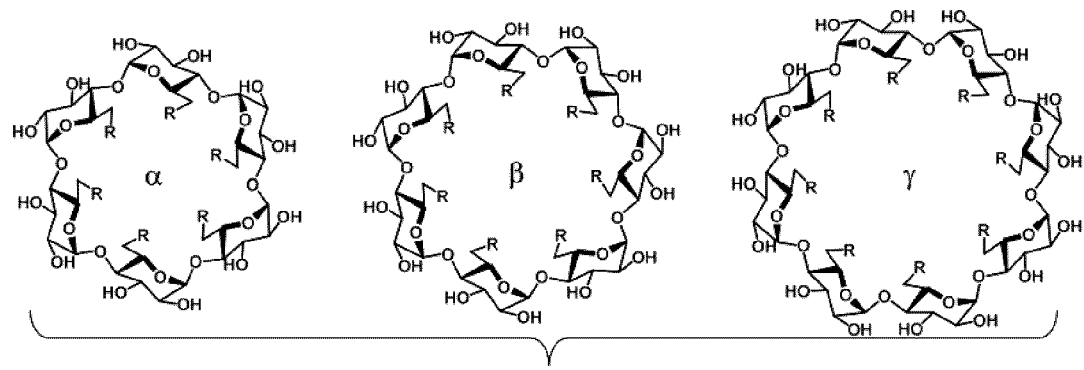
FIG. 9 shows an exemplary non-ionic analogs

FIG. 9 shows α, β and γ embodiments of CDs as described herein. In these embodiments, the 6-hydroxyl groups of native cyclodextrins are partially or completely replaced with R groups of the formula -G-L-X', such as —S-L-X', or with —OH. G, L and X' are defined above.

Figure 10:
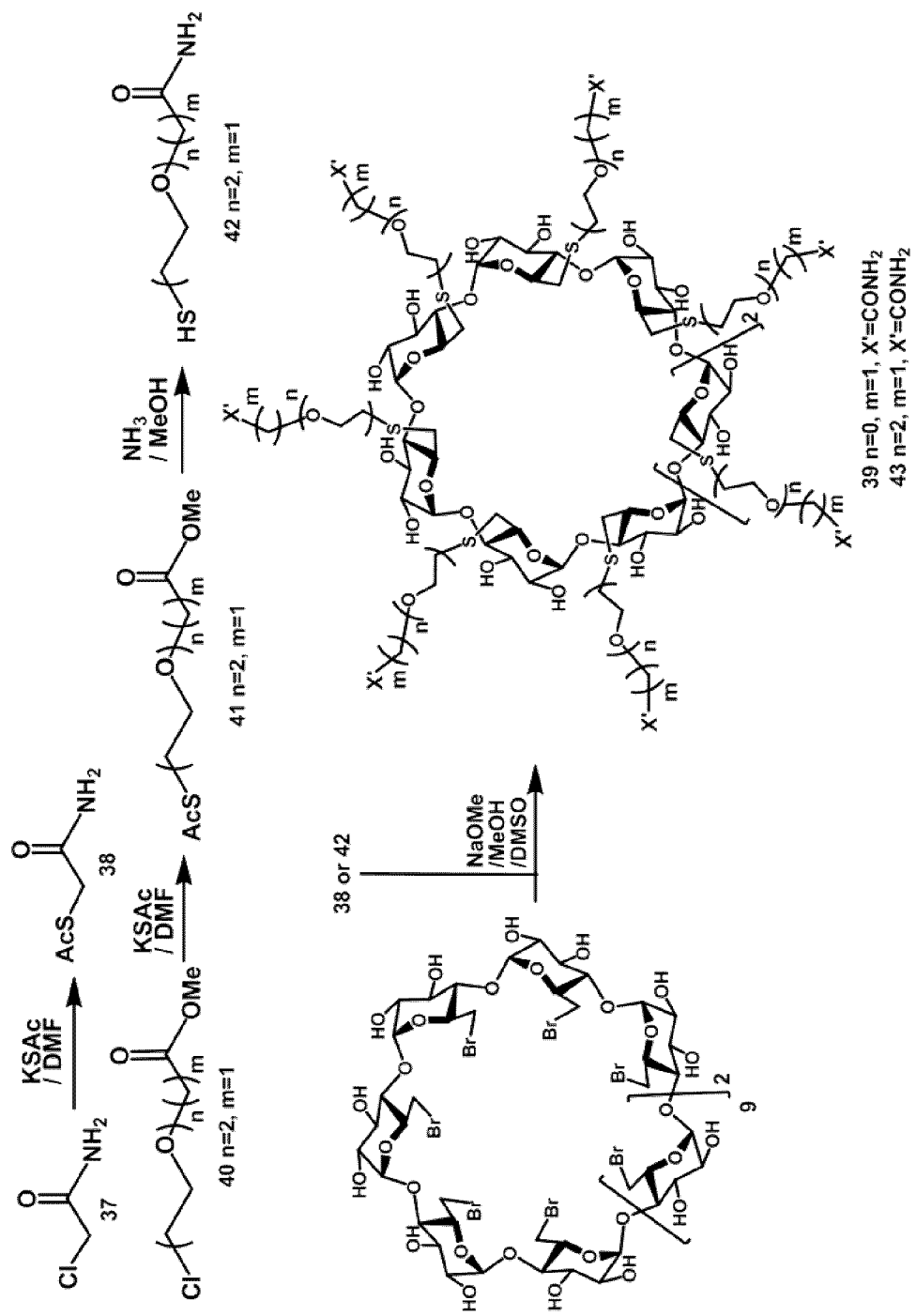
FIG. 10 shows an exemplary synthesis of non-ionic polyamide analogs containing PEG residues and preparation of the required reagents.

FIG. 10 shows an exemplary synthesis of non-ionic CDs. The reagents include the ω-haloalkanamide (such as the 2-chloroacetamide 37). The halide can be subsequently displaced with a thioacetate to afford the ω-(thioacetyl) alkanamide reagents (such as the 2-thioacetylacetamide 38). Additionally, ester analogs of the ω-haloalkanamide that have PEG chain embedded in any position of the ω-haloalkanoate chain (such as the ω-chlorinated ester 40) can be used. The terminal halide can be substituted with thioacetate to afford the ω-thioacetyl substituted esters (such as compound 41), and a subsequent aminolysis reaction simultaneously converts the ester functionality to the desired amide and also deprotect the thioacetyl group to the reactive thiol (such as compound 42). As with the polyanionic CD, the same 6-halogenated CD compounds can be used as a starting material for the subsequent nucleophilic substitutions. In this example, only a per-6-brominated gamma-CD is shown, but other per-6-halogented alpha- and beta-CD analogs may also be used for substitutions. As shown, the thioester 38 and thiol 42 were respectively subjected to a treatment with alkoxides in DMSO to generate an intermediate thiolates for reaction with the 6-brominated gamma-CD to obtain the non-ionic compounds 39 and a derivative 43 that has a PEG chain embedded into the linker.

Example 4: Properties of Synthesized SulfoPEG Polyanionic Derivatives 25-30

The synthesized SulfoPEG polyanionic derivatives 25-30 show some difference in their chemical properties.

Figure 11:
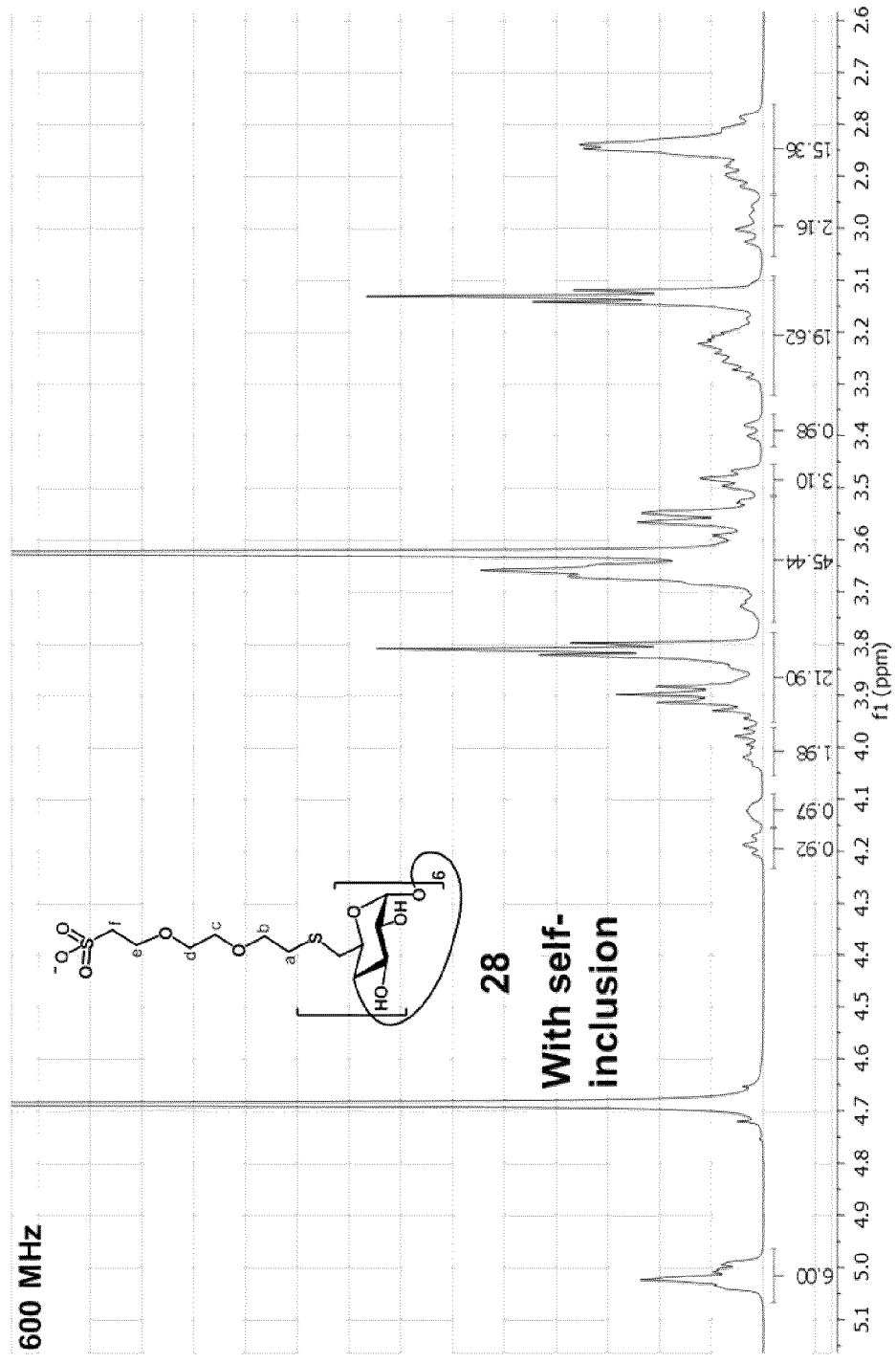
FIG. 11 shows an $^1$H NMR spectrum for a polyanionic α-CD derivative (structure 28).
Figure 12:
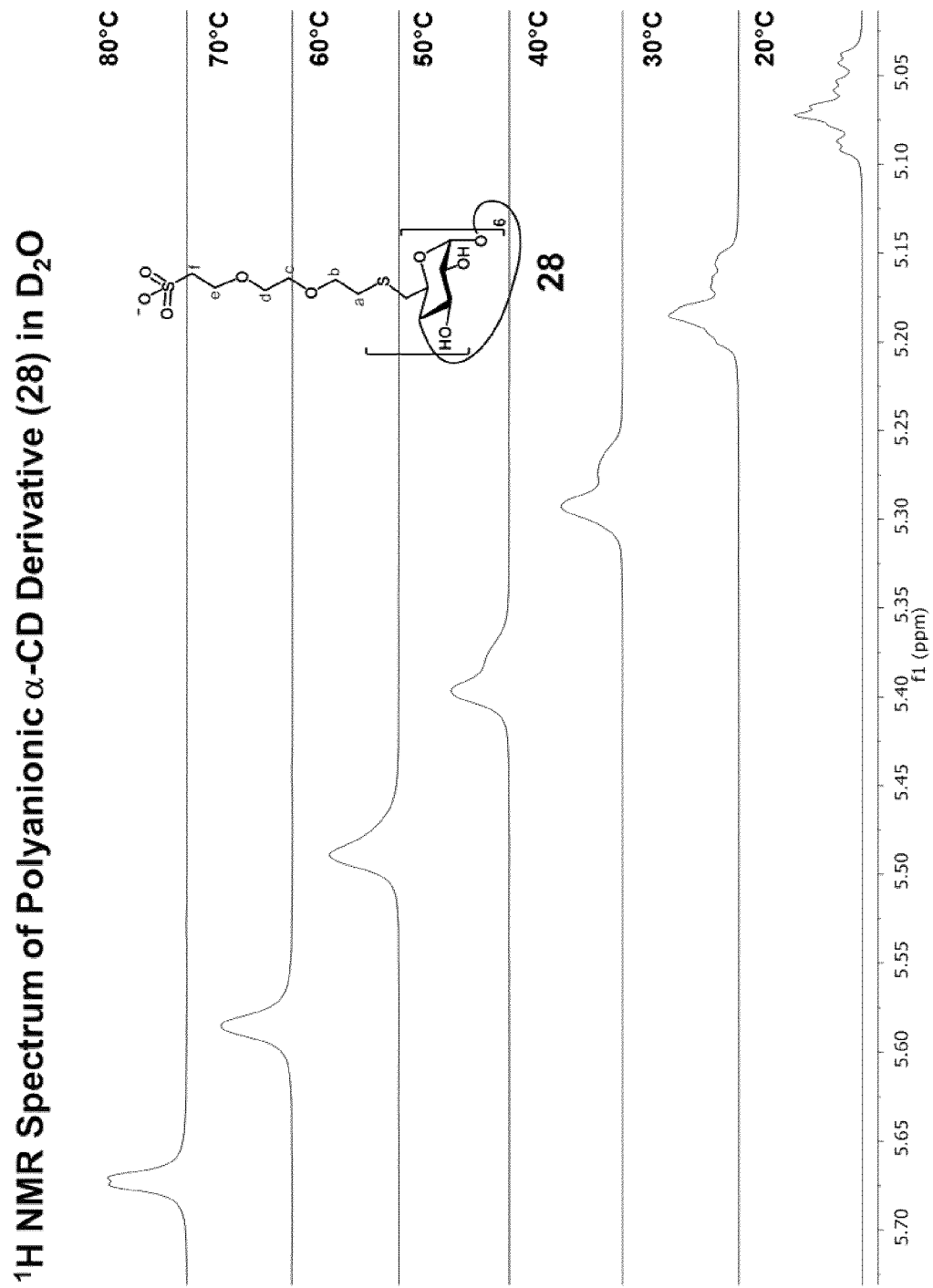
FIG. 12 shows variable temperature $^1$H NMR experiments of an α-CD derivative (structure 28).

FIGS. 11 and 12 show the $^1$H NMR spectra synthesized α-cyclodextrin derivative 28 which showed strong evidence of self-inclusion (one of its side arms bends and enters into the cavity of the molecule) at room temperature, as the observed $^1$H NMR spectra showed multiple types of glucosyl units. However, the $^1$H NMR spectra became increasingly simpler when the temperature was raised. At 80° C., the $^1$H NMR spectrum became symmetric, as only one type of the glucosyl unit was observed.

Figure 13:
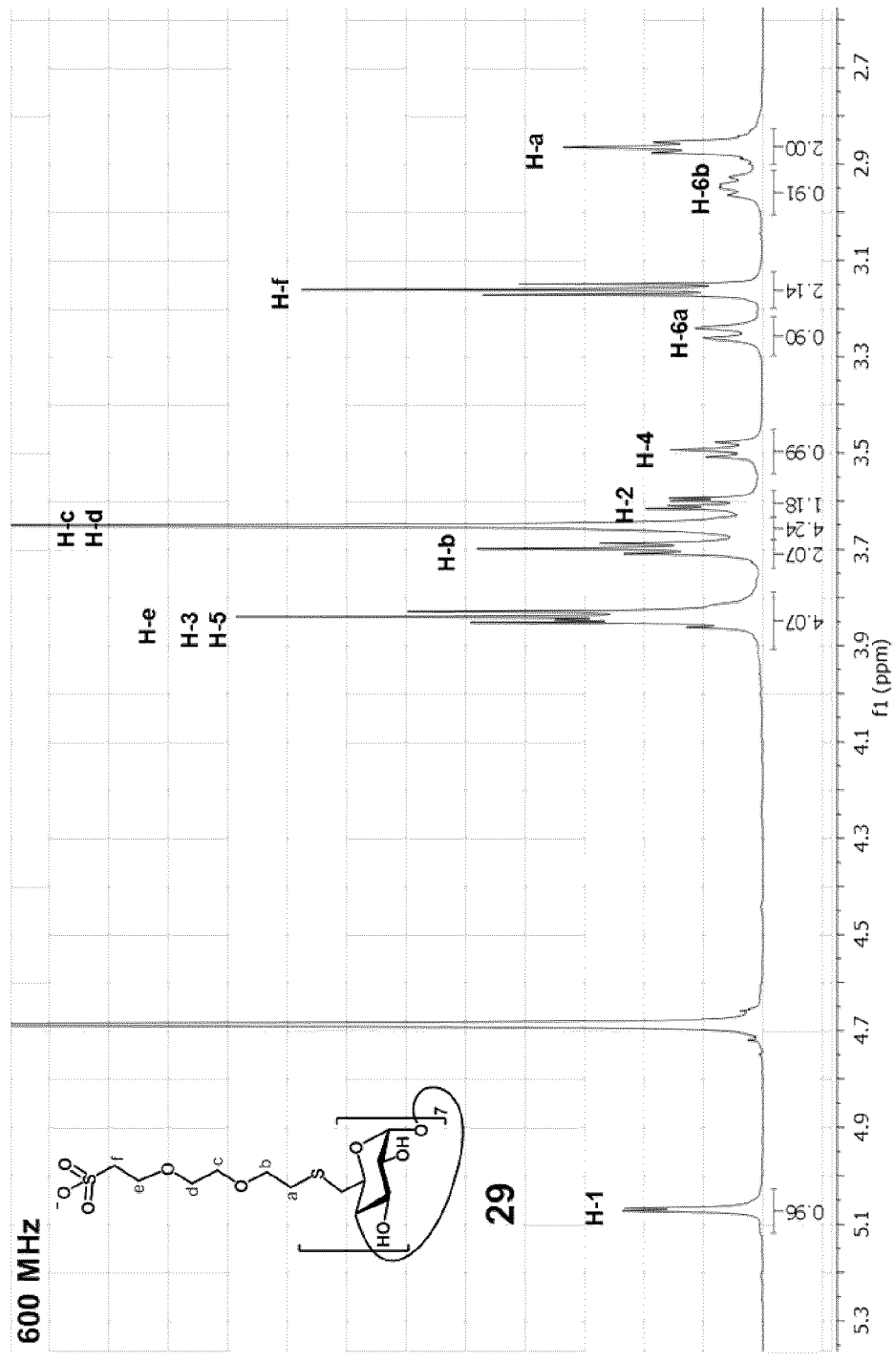
FIG. 13 shows an $^1$H NMR spectrum of polyanionic β-CD derivative (structure 29).
Figure 14:
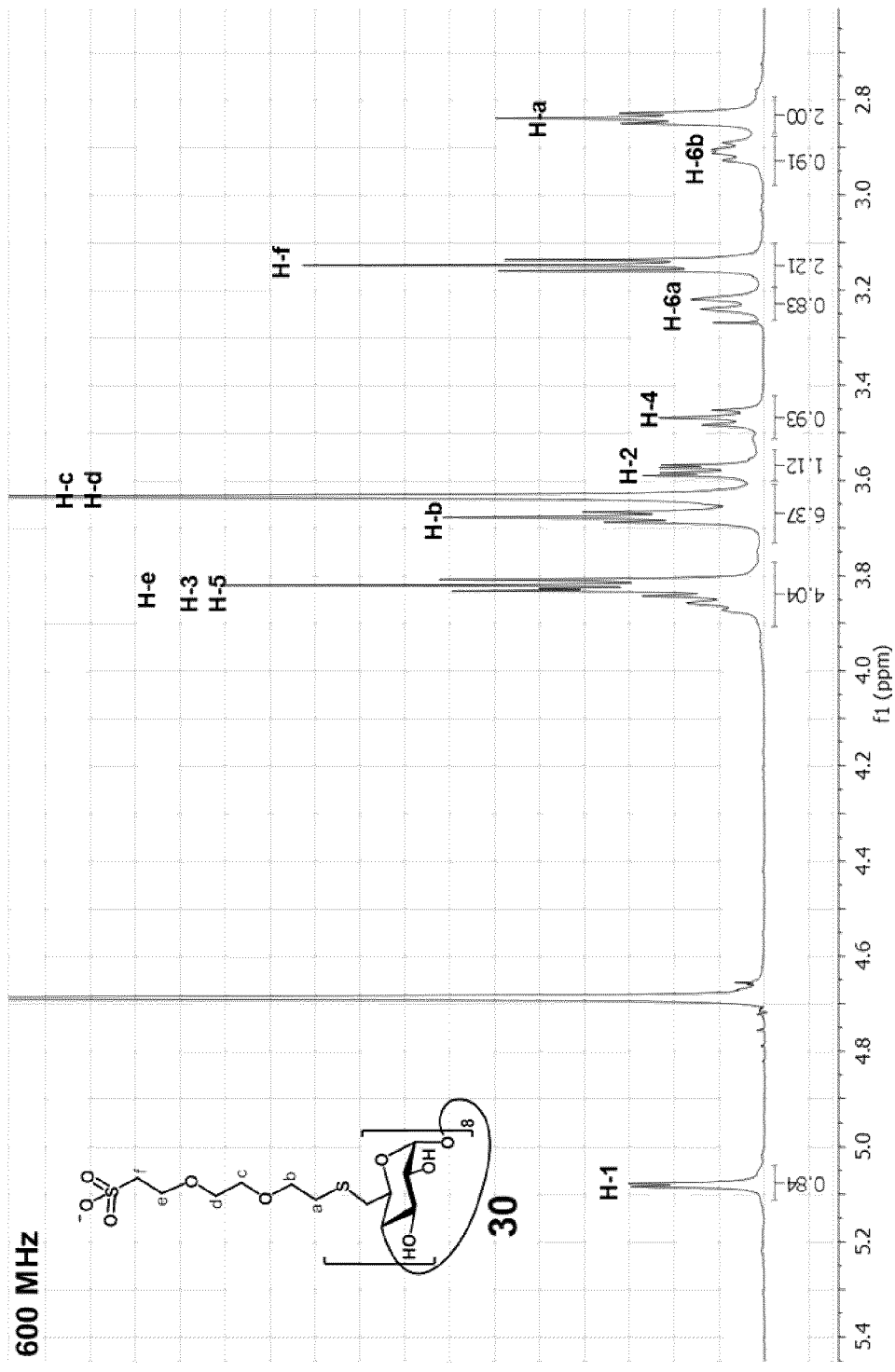
FIG. 14 shows an $^1$H NMR spectrum of polyanionic γ-CD derivative (structure 30).

However, no evidence of self-inclusion was observed for the other two sulfoPEG poluionic derivatives with a larger cavity (the β and γ-cyclodextrin derivatives 29-30). FIGS. 13 and 14 show the $^1$H NMR spectra of compound 29 and 30, respectively. Both recorded spectra were observed to be symmetric at room temperature.

Example 4: Properties of Synthesized Non-Ionic Derivatives 39

Figure 15:
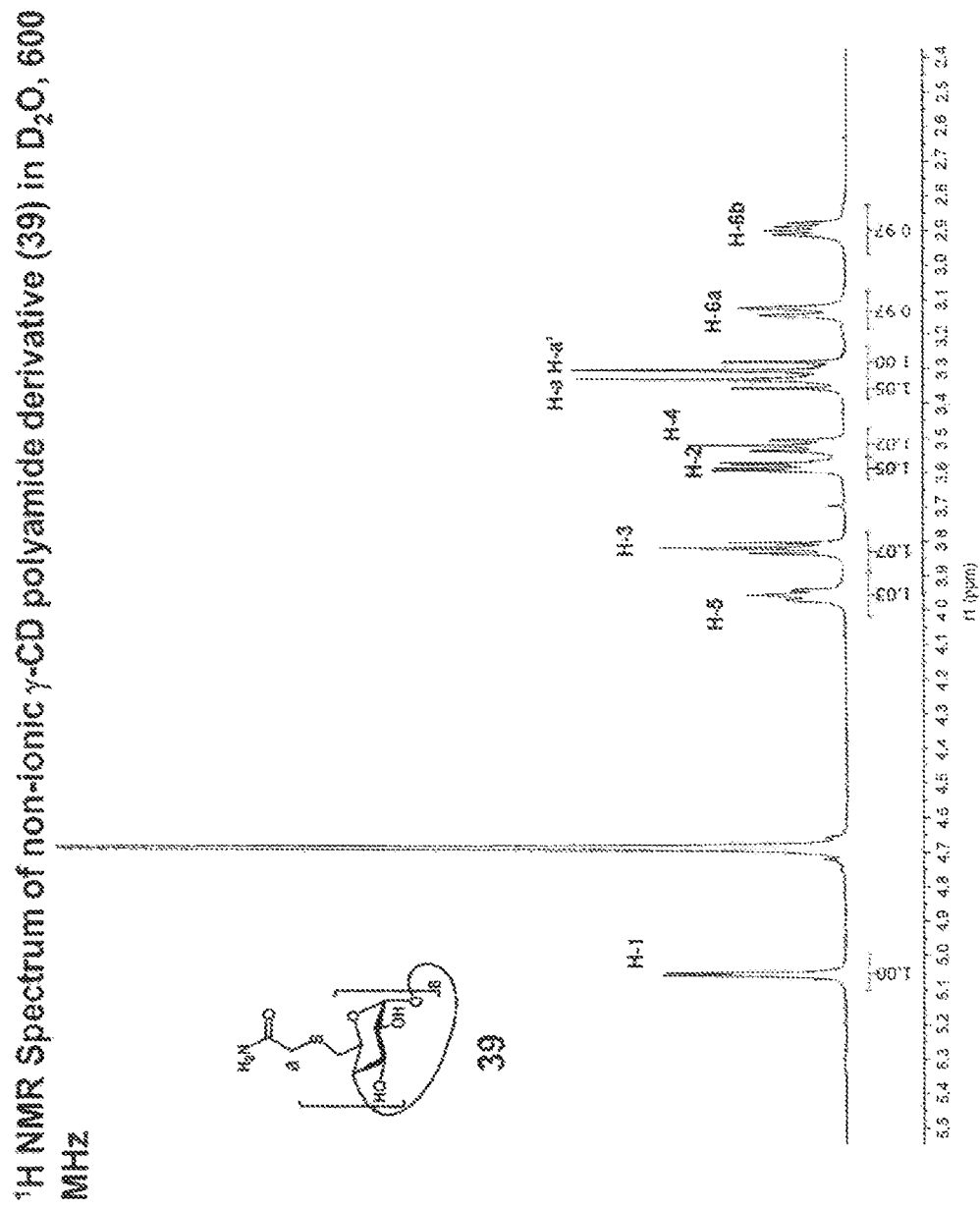
FIG. 15 shows an $^1$H NMR spectrum of non-ionic γ-CD polyamide derivative (structure 39).

FIG. 15 shows the $^1$H NMR spectrum of non-ionic gamma-cyclodextrin derivative 39 which showed the expected symmetry, as only one type of the glucosyl unit was observed.

Figure 16:
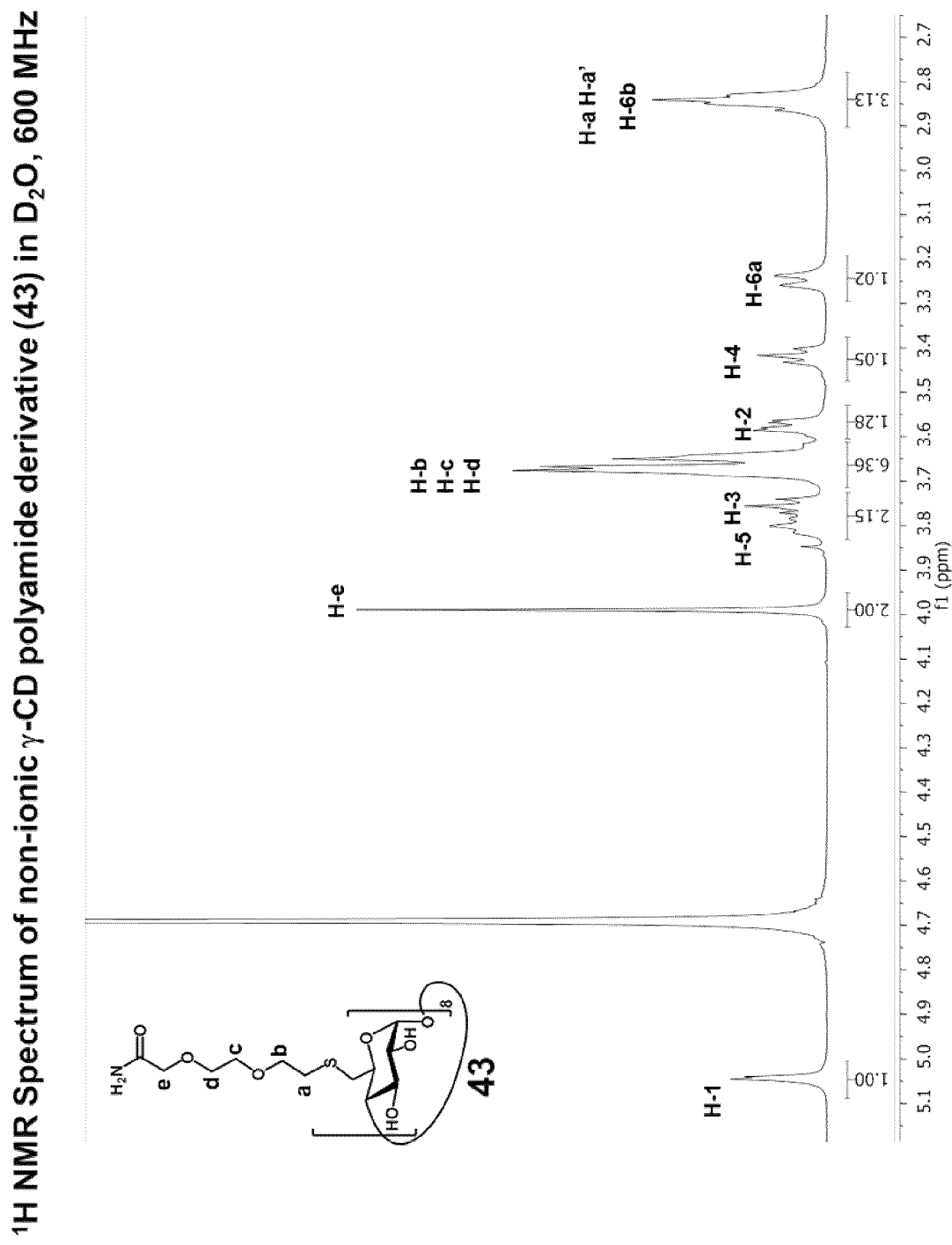
FIG. 16 shows an $^1$H NMR spectrum of non-ionic PEGylated γ-CD polyamide derivative (structure 43).

FIG. 16 shows the $^1$H NMR spectrum of non-ionic gamma-cyclodextrin derivative 43 which showed the expected symmetry as well as the PEG group. Only one type of the glucosyl unit was observed.

Example 5: Inclusion Studies

Inclusion studies were conducted to determine whether the CD-based polyanionic SulfoPEG thioether described herein are suitable for carrying a guest molecule.

Figure 17:
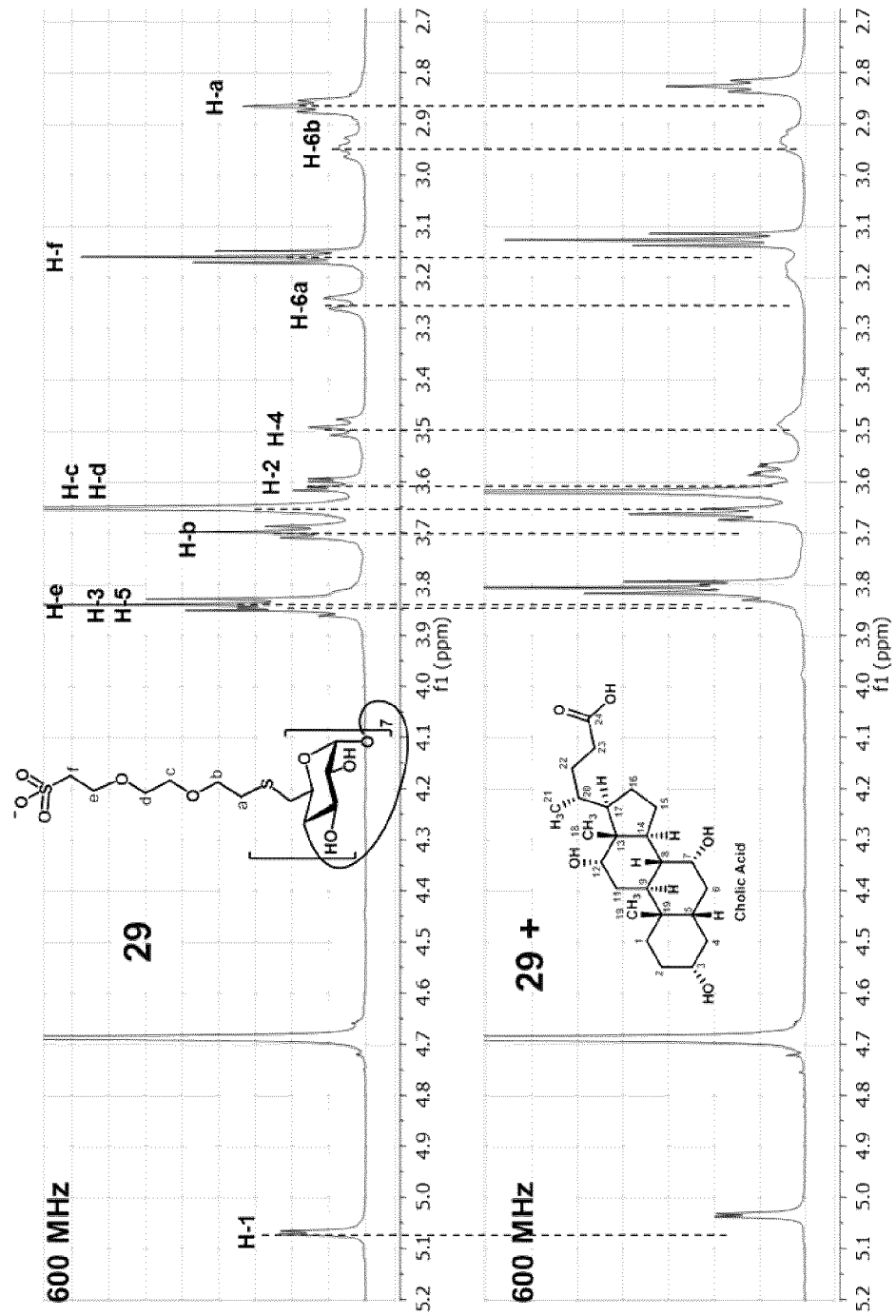
FIG. 17 shows an $^1$H NMR spectrum of polyanionic β-CD derivative (structure 29) forming an inclusion complex with cholic acid.

FIG. 17 shows the inclusion studies of sulfoPEG β-cyclodextrin derivatives 29. In these studies, the polyanionic β-CD compound (29) was analyzed both without (top panel) and with (bottom panel) cholic acid included within the CD compound. The results show that a polyanionic CD compound in accordance with the present invention can be used as a carrier of guest molecules. However, it can be contemplated that other polyanionic and non-ionic CD compounds as described herein may also be suitable as a carrier or excipient with other guest molecules.

Figure 18:
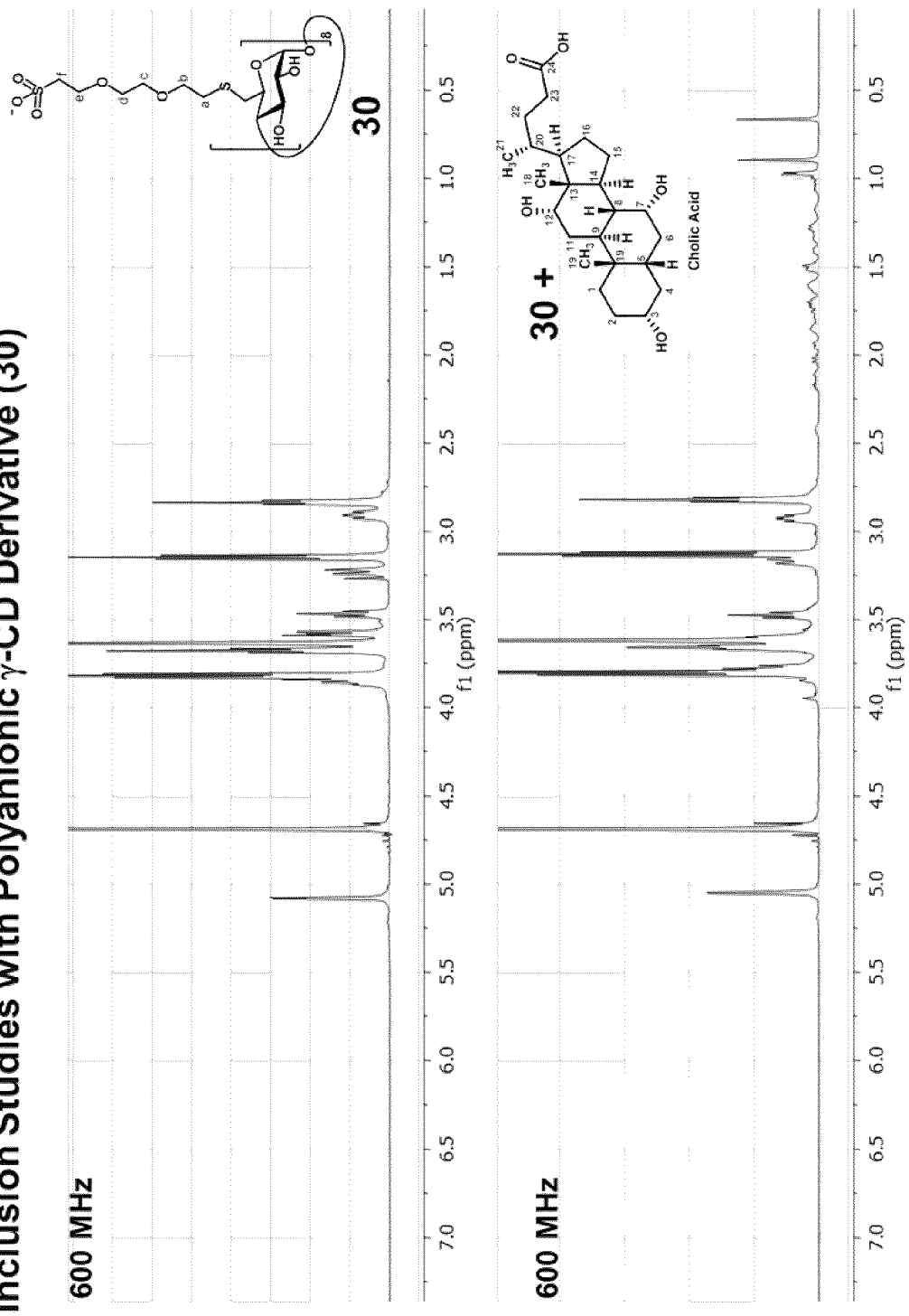
FIG. 18 shows an $^1$H NMR spectrum of polyanionic γ-CD derivative (structure 30) forming an inclusion complex with cholic acid.
Figure 19:
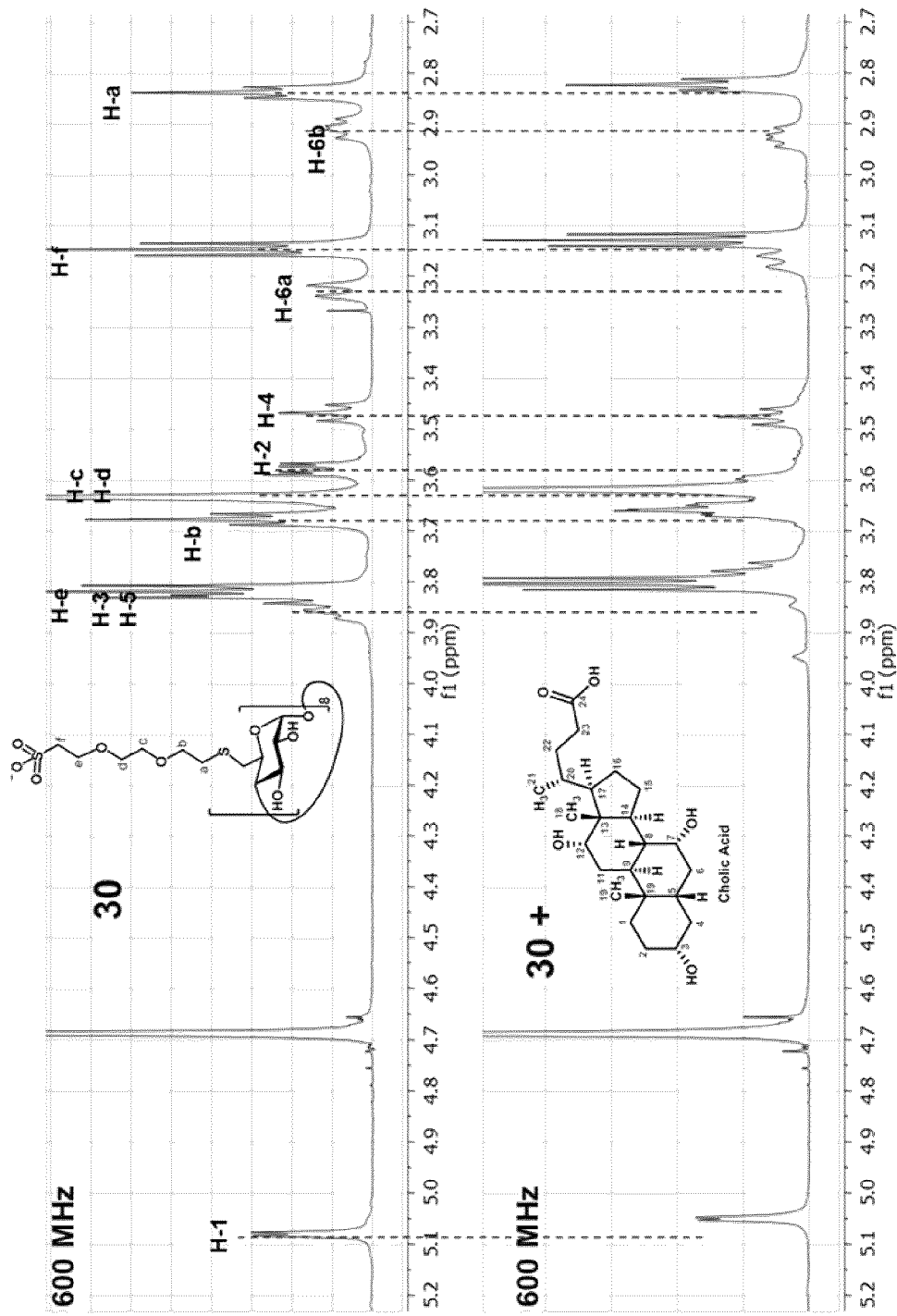
FIG. 19 shows the expanded $^1$H NMR spectrum of the polyanionic γ-CD derivative (structure 30) forming an inclusion complex with cholic acid.

FIGS. 18 and 19 show similar inclusion studies of sulfoPEG γ-cyclodextrin derivative 30 with cholic acid (top panel: compound 30 alone, bottom panel: compound 30 with cholic acid).

Therefore, the present experiments provide exemplary polyanionic and non-ionic CD-based compounds which can be used as excipients and/or carriers of guest molecules in a number of pharmaceutical applications.

REFERENCES

U.S. Pat. No. 7,632,941, Defaye, J., et al., Cyclodextrin Derivatives, Method for the Preparation thereof and Use thereof for the Solubilization of Pharmacologically Active Substances.

U.S. Ser. No. 12/374,211, Defaye, J. (Centre National de la Recherche Scientifique), Novel Amphiphilic Cyclodextrin Derivatives.

PCT/FR2004/000691, Defaye, J. (Centre National de la Recherche Scientifique), Novel Cyclodextrin Derivatives, Methods for Preparation Thereof and use for the Solubilization of Pharmacologically Active Substances.

U.S. Pat. No. 6,670,340, 6-Mercapto-Cyclodextrin Derivatives: Reversal Agents for Drug-Induced Neuromuscular Block.

U.S. Pat. No. 6,949,527, 6-Mercapto-Cyclodextrin Derivatives: Reversal Agents for Drug-Induced Neuromuscular Block.

DE 102010012281, Bichimaier, I., Pharmazeutische zusammensetzungen enthaltend substituiertes 6-deoxy-6-sulfanylcyclodextrin.

Bull. Chem. Soc. Chim. Fr. 132 (8), 857-866, 1995.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A polyanionic cyclodextrin-based compound of Formula II

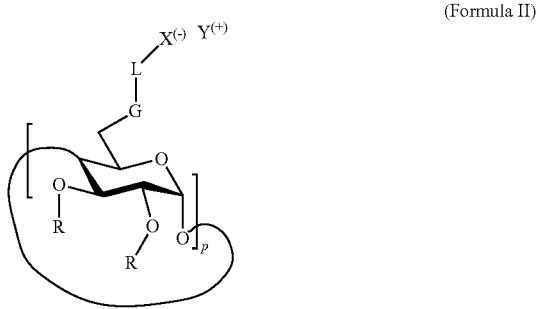

(Formula II)

wherein $X^{(-)}$ is $SO_3^-$;

$Y^{(+)}$ is one or more counter cations;

L is

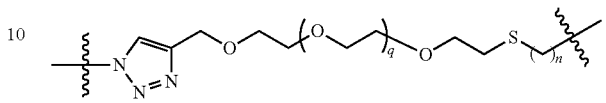

where q is 0 to 20 and n is 1-5;

G is a bond;

p is 6 (α-cyclodextrin), 7 (β-cyclodextrin) or 8 (γ-cyclodextrin); and

R is H or an optionally substituted C1-C18 alkyl or an optionally substituted acyl group.

2. The compound of claim 1, wherein $Y^{(+)}$ is a pharmaceutically acceptable cation.

3. The compound of claim 2, where $Y^{(+)}$ is $Na^+$ or $K^+$.

4. The compound of claim 1, wherein R is H, an optionally substituted $C_1$-$C_{18}$ alkyl group, or optionally substituted $C_1$-$C_{18}$ acyl group.

5. A pharmaceutical composition comprising a medicament and the compound of claim 1.

6. An excipient comprising the compound of claim 1.

* * * * *